(12) United States Patent
Woyke et al.

(10) Patent No.: US 12,613,230 B2
(45) Date of Patent: Apr. 28, 2026

(54) DEVICE AND PROCESS FOR ANALYSING GAS EFFECTS IN SAMPLES

(71) Applicants: Medizinische Universität Innsbruck, Innsbruck (AT); EURAC RESEARCH, Bolzano (IT)

(72) Inventors: Simon Woyke, Innsbruck (AT); Thomas Haller, Innsbruck (AT)

(73) Assignees: Medizinische Universität Innsbruck, Innsbruck (AT); Eurac Research, Bolzano (IT)

( * ) Notice: Subject to any disclaimer, the term of this patent is extended or adjusted under 35 U.S.C. 154(b) by 314 days.

(21) Appl. No.: 18/250,790

(22) PCT Filed: Oct. 21, 2021

(86) PCT No.: PCT/EP2021/079295
§ 371 (c)(1),
(2) Date: Apr. 27, 2023

(87) PCT Pub. No.: WO2022/090062
PCT Pub. Date: May 5, 2022

(65) Prior Publication Data
US 2023/0408474 A1 Dec. 21, 2023

(30) Foreign Application Priority Data
Oct. 27, 2020 (EP) .................................... 20204184

(51) Int. Cl.
*G01N 33/00* (2006.01)
*G01J 3/02* (2006.01)
(52) U.S. Cl.
CPC ........ *G01N 33/0062* (2013.01); *G01J 3/0202* (2013.01); *G01N 33/0031* (2013.01); *G01N 33/0036* (2013.01)

(58) Field of Classification Search
CPC .. G01N 21/3504; G01N 21/39; G01N 33/004; G01N 33/0006; G01N 27/12;
(Continued)

(56) References Cited

U.S. PATENT DOCUMENTS 7,257,987 B2 * 8/2007 O'Brien ............... G01N 1/2202
73/23.22
10,173,217 B2 1/2019 Yamawaki et al.
(Continued)

FOREIGN PATENT DOCUMENTS

EP 2784481 A2 10/2014
EP 3216518 A1 * 9/2017 ........ B01L 3/502784
(Continued)

OTHER PUBLICATIONS

Arain, et al., "Characterization of microtiterplates with integrated optical sensors for oxygen and pH, and their applications to enzyme activity screening, respirometry, and toxicological assays", 2005, Sensors and Actuators, vol. B 113, pp. 639-648.
(Continued)

*Primary Examiner* — Andre J Allen
(74) *Attorney, Agent, or Firm* — Greer, Burns & Crain, Ltd.; Steven P. Fallon

(57) ABSTRACT

The invention provides a device and a process for analysing the effect of a concentration of a gas on a sample, especially measurement of the gas concentration within a sample, and/or measurement of the effect of the absorption and/or desorption of a gas by the sample, using spectrophotometric detection of a gas-sensitive and optically detectable analyte of the sample while measuring the concentration of the gas in a gas composition that is continuously delivered to each sample well in order to contact the samples with a gas
(Continued)

having a predetermined and/or measured concentration, respectively a pre-determined and/or measured partial pressure.

19 Claims, 6 Drawing Sheets

(58) Field of Classification Search
CPC .............. G01N 21/01; G01N 33/0004; G01N 33/0031; G01N 33/497; G01N 21/31; G01N 33/0009; G01N 33/0037; G01N 33/0036; G01N 27/127; G01N 33/0047; G01N 27/4074; G01N 33/0063; G01N 27/419; G01N 2021/399; G01N 27/407; G01N 33/0062; G01N 27/125; G01N 21/1702; G01N 33/005; G01N 27/4071; G01N 1/24; G01N 21/274; G01N 2021/1704; G01N 21/031; G01N 33/0027; G01N 27/16; G01N 27/4077; G01N 27/4075; G01N 21/61; G01N 15/06; G01N 33/007; G01N 21/783; G01N 27/4067; G01N 27/41; G01N 21/33; G01N 2291/02809; G01N 33/00; G01N 30/02; G01N 27/4045; G01N 21/314; G01N 27/409; G01N 29/024; G01N 27/26; G01N 27/4065; G01N 33/0073; G01N 1/22; G01N 2021/0112; G01N 33/0054; G01N 27/4175; G01N 21/359; G01N 27/128; G01N 33/0011; G01N 33/0067; G01N 33/0016; G01N 27/18; G01N 21/0303; G01N 33/225; G01N 27/00; G01N 27/122; G01N 27/404; G01N 21/05; G01N 2291/021; G01N 33/0044; G01N 33/0075; G01N 27/4163; G01N 25/18; G01N 1/34; G01N 21/3518; G01N 29/036; G01N 29/022; G01N 27/416; G01N 33/2841; G01N 1/2273; G01N 1/28; G01N 27/4141; G01N 2021/3513; G01N 21/27; G01N 21/255; G01N 27/123; G01N 2291/0215; G01N 27/417; G01N 33/4975; G01N 21/85; G01N 21/65; G01N 2030/025; G01N 27/04; G01N 27/4073; G01N 2021/3595; G01N 21/25; G01N 21/03; G01N 1/38; G01N 33/0042; G01N 31/12; G01N 27/4072; G01N 27/4162; G01N 15/075; G01N 33/4972; G01N 1/2205; G01N 2201/06113; G01N 2021/1793; G01N 30/06; G01N 1/2226; G01N 29/222; G01N 21/59; G01N 33/0032; G01N 33/24; G01N 2291/02836; G01N 2201/0221; G01N 21/15; G01N 21/7703; G01N 21/17; G01N 1/2252; G01N 1/2247; G01N 2021/8578; G01N 2021/3531; G01N 27/126; G01N 21/45; G01N 33/0065; G01N 33/0068; G01N 27/30; G01N 27/4076; G01N 2021/7786; G01N 2201/0612; G01N 21/35; G01N 27/62; G01N 2021/1795; G01N 2291/0212; G01N 21/84; G01N 33/0034; G01N 2015/0046; G01N 2021/391; G01N 27/124; G01N 33/18; G01N 27/4078; G01N 29/02; G01N 21/6428; G01N 2201/1211; G01N 1/4077; G01N 21/643; G01N 33/0014; G01N 21/64; G01N 21/37; G01N 33/0039; G01N 1/44; G01N 33/4925; G01N 31/223; G01N 27/129; G01N 27/14; G01N 33/02; G01N 30/88; G01N 27/66; G01N 1/26; G01N 21/3151; G01N 2201/08; G01N 2001/4016; G01N 2001/4088; G01N 29/2418; G01N 2201/0636; G01N 2291/0256; G01N 31/10; G01N 1/2294; G01N 1/2258; G01N 13/00; G01N 29/326; G01N 27/121; G01N 2201/062; G01N 29/2425; G01N 1/4005; G01N 1/405; G01N 27/301; G01N 27/4146; G01N 21/78; G01N 21/3103; G01N 1/2214; G01N 33/0018; G01N 31/22; G01N 21/8507; G01N 2013/003; G01N 25/20; G01N 33/0059; G01N 33/0057; G01N 33/491; G01N 21/53; G01N 21/77; G01N 2021/3129; G01N 21/0332; G01N 2291/02881; G01N 33/2823; G01N 33/0013; G01N 2201/127; G01N 33/0022; G01N 2021/0314; G01N 2291/048; G01N 15/08; G01N 2021/6432; G01N 21/00; G01N 33/0072; G01N 17/00; G01N 27/622; G01N 7/00; G01N 2021/151; G01N 33/0026; G01N 2291/0427; G01N 21/41; G01N 5/02; G01N 27/223; G01N 15/0826; G01N 2291/011; G01N 27/403; G01N 27/227; G01N 2021/3166; G01N 33/006; G01N 21/552; G01N 2291/014; G01N 21/276; G01N 29/032; G01N 15/082; G01N 27/226; G01N 2201/0691; G01N 25/54; G01N 21/80; G01N 2291/02818; G01N 30/72; G01N 27/4062; G01N 25/00; G01N 2027/222; G01N 27/64; G01N 2201/061; G01N 25/22; G01N 27/414; G01N 33/0029; G01N 27/02; G01N 21/3577; G01N 1/40; G01N 2021/3545; G01N 7/10; G01N 1/2202; G01N 2201/068; G01N 33/2025; G01N 21/1717; G01N 27/221; G01N 2021/3133; G01N 27/4148; G01N 29/30; G01N 27/406; G01N 27/22; G01N 33/0008; G01N 2021/7773; G01N 30/7206; G01N 15/0656; G01N 2291/0423; G01N 33/241; G01N 15/02; G01N 2021/3137; G01N 2021/772; G01N 27/413; G01N 2015/1006; G01N 2291/102; G01N 31/224; G01N 7/14; G01N 2021/158; G01N 27/4143; G01N 2021/1708; G01N 2021/458; G01N 2201/12; G01N 2201/1218; G01N 25/32; G01N 17/002; G01N 2015/1486; G01N 21/645; G01N 2201/1215; G01N 1/10; G01N 27/045; G01N 33/0001; G01N 33/28; G01N 27/041; G01N 27/626; G01N 2001/2893; G01N 30/00; G01N 2021/396; G01N 21/3581; G01N 21/09; G01N 33/22; G01N 2001/2264; G01N 21/90; G01N 21/171; G01N 33/4977; G01N 27/27; G01N 2001/021; G01N 21/94; G01N 33/48; G01N 30/66; G01N 33/227; G01N 2021/3181; G01N 27/74; G01N 2021/317; G01N 21/658; G01N 2201/129; G01N 2021/3155; G01N 21/5907; G01N 33/5005; G01N
2001/2244; G01N 2021/7783; G01N
15/0205; G01N 27/40; G01N 30/12;
G01N 7/04; G01N 1/00; G01N 21/49;
G01N 21/6408; G01N 35/00; G01N
21/21; G01N 33/0098; G01N 15/1459;
G01N 30/08; G01N 31/225; G01N 35/10;
G01N 15/1433; G01N 1/14; G01N 15/00;
G01N 2001/2229; G01N 21/3563; G01N
21/55; G01N 2001/2223; G01N
2015/084; G01N 30/64; G01N
2201/0214; G01N 33/222; G01N
21/3554; G01N 2021/052; G01N 21/11;
G01N 21/6486; G01N 2291/02872; G01N
15/1434; G01N 21/75; G01N 21/76;
G01N 2201/0231; G01N 27/308; G01N
33/84; G01N 2201/0627; G01N 15/0806;
G01N 21/766; G01N 2291/0426; G01N
2021/0346; G01N 22/00; G01N 29/4472;
G01N 27/304; G01N 27/185; G01N
33/14; G01N 2291/0255; G01N 29/32;
G01N 33/1826; G01N 2291/02433; G01N
27/228; G01N 30/30; G01N 27/026;
G01N 30/68; G01N 5/0211; G01N
2030/8854; G01N 33/0019; G01N 30/20;
G01N 33/0049; G01N 15/1436; G01N
27/70; G01N 33/025; G01N 35/00871;
G01N 2021/3536; G01N 21/553; G01N
27/046; G01N 27/06; G01N 30/14; G01N
15/088; G01N 29/4436; G01N 29/46;
G01N 33/5308; G01N 27/028; G01N
30/74; G01N 33/98; G01N 2201/0668;
G01N 21/6402; G01N 1/4022; G01N
2001/245; G01N 2035/00326; G01N
21/554; G01N 21/8483; G01N
2201/0696; G01N 2021/6434; G01N
21/67; G01N 33/0021; G01N 2001/2241;
G01N 25/56; G01N 29/348; G01N
31/005; G01N 33/56922; G01N
2021/3509; G01N 2291/101; G01N
5/00584; G01N 27/49; G01N 27/623;
G01N 33/0024; G01N 2001/2255; G01N
33/5438; G01N 2001/2282; G01N 30/16;
G01N 33/0052; G01N 9/36; G01N
17/006; G01N 2333/195; G01N 33/146;
G01N 2021/8521; G01N 33/15; G01N
2021/394; G01N 21/73; G01N 25/30;
G01N 29/323; G01N 15/01; G01N
2021/3148; G01N 21/51; G01N
2291/0217; G01N 25/28; G01N 25/36;
G01N 2021/3174; G01N 2291/105; G01N
27/28; G01N 17/02; G01N 21/4133;
G01N 21/47; G01N 31/221; G01N
2001/2261; G01N 2021/8416; G01N
21/253; G01N 31/00; G01N 5/04; G01N
15/14; G01N 2021/3125; G01N
2201/0662; G01N 29/2462; G01N 1/42;
G01N 2035/00356; G01N 33/0055; G01N
2001/2217; G01N 2001/227; G01N
2001/2276; G01N 2001/2285; G01N
35/0092; G01N 15/0618; G01N
2021/4709; G01N 2021/773; G01N
15/1429; G01N 2021/0389; G01N 21/63;
G01N 21/71; G01N 2201/121; G01N
25/4873; G01N 33/50; G01N 35/04;

G01N 2021/6417; G01N 2201/066; G01N
25/66; G01N 27/48; G01N 33/54373;
G01N 29/14; G01N 29/22; G01N 29/36;
G01N 30/6095; G01N 9/00; G01N
2001/386; G01N 2021/157; G01N
2021/536; G01N 21/68; G01N 21/9081;
G01N 2201/024; G01N 2201/088; G01N
35/0099; G01N 2021/354; G01N
2030/642; G01N 21/718; G01N
2201/0686; G01N 2201/0697; G01N
2291/02845; G01N 3/02; G01N 33/205;
G01N 5/00; G01N 2021/6484; G01N
2021/8557; G01N 2201/06186; G01N
30/78; G01N 33/54366; G01N 17/04;
G01N 2021/8405; G01N 2021/8411;
G01N 2201/023; G01N 2201/1296; G01N
2291/015; G01N 27/333; G01N 27/4145;
G01N 35/08; G01N 2021/3185; G01N
2291/044; G01N 29/343; G01N 29/44;
G01N 3/08; G01N 15/1404; G01N
2021/451; G01N 21/532; G01N 30/86;
G01N 33/492; G01N 35/00693; G01N
35/1002; G01N 15/0255; G01N
2015/086; G01N 2021/775; G01N
2201/084; G01N 2021/0364; G01N
2021/0378; G01N 2201/025; G01N
2201/0633; G01N 2291/012; G01N
25/72; G01N 30/32; G01N 2015/1493;
G01N 27/3278; G01N 1/286; G01N
21/534; G01N 30/8675; G01N 33/1846;
G01N 2021/6439; G01N 21/774; G01N
30/8665; G01N 13/04; G01N 21/3586;
G01N 27/225; G01N 27/68; G01N
29/4463; G01N 33/0096; G01N 35/025;
G01N 1/08; G01N 2015/0866; G01N
2291/045; G01N 30/96; G01N 33/5008;
G01N 2021/0307; G01N 2030/062; G01N
21/648; G01N 2201/126; G01N
2203/0019; G01N 27/327; G01N 33/49;
G01N 2030/121; G01N 29/2437; G01N
33/53; G01N 35/026; G01N 35/1009;
G01N 35/1065; G01N 2001/4066; G01N
2021/3159; G01N 2030/085; G01N
25/4893; G01N 27/60; G01N 29/38;
G01N 29/4427; G01N 33/4833; G01N
2001/2279; G01N 27/205; G01N
33/56911; G01N 15/0893; G01N 15/149;
G01N 2021/1748; G01N 2021/3196;
G01N 27/624; G01N 29/34; G01N 3/12;
G01N 2021/0385; G01N 2030/123; G01N
23/2273; G01N 33/487; G01N 33/569;
G01N 33/96; G01N 35/028; G01N
1/2211; G01N 2015/1497; G01N
2021/0193; G01N 2021/058; G01N
2030/146; G01N 2035/00881; G01N
21/278; G01N 21/6452; G01N 21/8422;
G01N 2201/12753; G01N 29/42; G01N
33/287; G01N 9/002; G01N 1/2208;
G01N 19/00; G01N 2021/3177; G01N
2021/392; G01N 2021/651; G01N
2021/7776; G01N 2021/8466; G01N
2030/128; G01N 2035/00495; G01N
2291/02863; G01N 29/2406; G01N
30/34; G01N 33/383; G01N 33/5023;
G01N 33/56983; G01N 2001/2232; G01N

21/72; G01N 2201/0631; G01N 2201/0634; G01N 33/2888; G01N 33/4915; G01N 33/493; G01N 2021/0106; G01N 2021/7759; G01N 2035/0418; G01N 21/6458; G01N 2201/12746; G01N 27/4035; G01N 27/4165; G01N 7/16; G01N 1/2035; G01N 2015/0662; G01N 2015/1029; G01N 2021/1725; G01N 2021/7709; G01N 21/66; G01N 2201/0216; G01N 2469/20; G01N 29/2431; G01N 30/84; G01N 15/147; G01N 2015/0026; G01N 2021/653; G01N 2030/065; G01N 2030/884; G01N 2030/8881; G01N 2030/8886; G01N 27/4114; G01N 29/00; G01N 33/554; G01N 1/02; G01N 11/00; G01N 15/1031; G01N 2001/022; G01N 21/763; G01N 21/7746; G01N 21/9501; G01N 2201/0873; G01N 27/07

See application file for complete search history.

(56) References Cited

U.S. PATENT DOCUMENTS

| | | | | |
|---|---|---|---|---|
| 2003/0049862 | A1* | 3/2003 | He | B01L 3/50853 |
| | | | | 422/82.11 |
| 2003/0190608 | A1* | 10/2003 | Blackburn | B01L 3/50273 |
| | | | | 435/7.1 |
| 2004/0035183 | A1* | 2/2004 | O'Brien | G01N 1/2202 |
| | | | | 73/431 |
| 2014/0273191 | A1 | 9/2014 | Tipgunlakant et al. | |

FOREIGN PATENT DOCUMENTS

| | | | | |
|---|---|---|---|---|
| WO | WO-9612182 A1 * | 4/1996 | | G01N 33/0024 |
| WO | 02/14539 A1 | 2/2002 | | |

OTHER PUBLICATIONS

Grist, et al., "Microfluidic cell culture systems with integrated sensors for drug screening", 2012, Proc. of SPIE, vol. 8251, pp. 825103-1-825103-12.

Guarnone, et al., "Performance Characteristics of Hemox-Analyzer for Assessment of the Hemoglobin Dissociation Curve", 1995, Haematologica, vol. 80, pp. 426-430.

Patel, et al., "Development and validation of an oxygen dissociation assay, a screening platform for discovering, and characterizing hemoglobin-oxygen affinity modifiers", 2018, Drug Design, Development and Therapy, vol. 12, pp. 1599-1607.

Sick, et al., "Continuous Gas-Depletion Technique for Measuring $O_2$-Dissociation Curves of High-Affinity Hemoglobins", 1985, Analytical Biochemistry, vol. 146, pp. 277-280.

Wang, et al., "Optical methods for sensing and imaging oxygen: materials, spectroscopies and applications", 2014, Chem Soc. Rev., vol. 43, pp. 3666-3761.

International Search Report from the corresponding International Patent Application No. PCT/EP2021/079295, dated Dec. 15, 2021.

* cited by examiner 4-channel system

Oxygen partial pressure, PO₂ (kPa)

DEVICE AND PROCESS FOR ANALYSING GAS EFFECTS IN SAMPLES

The present application provides a process and a device suitable for use in the process for analysing the effects of a concentration of a gas in a sample, which can be liquid or solid. The device and the process have the advantage of providing detailed measurement results while using a small sample volume of the sample to be analysed, and to enable the analysis of a number of samples within a short time, e.g. analysing a number of samples in parallel. The gas preferably is a gas component of a gas composition. A liquid sample can comprise particles, e.g. vesicles or solids, e.g. in suspension, preferably a liquid sample contains cells, e.g. in suspension or adherent to a surface e.g. of a sample well. A solid sample can comprise solid particles, e.g. a powder or a solid of one or more constituents, e.g. a lyophilized sample.

Herein, analysing the effect of the concentration of a gas on a sample may comprise the measurement of the gas concentration within the sample, and/or measurement of the absorption and/or desorption of gas by the sample. In a preferred embodiment, the device is set up for a process that for the sample determines the desorption and/or absorption capacity of gas, and/or respectively the absorption and/or desorption capacity of gas. In a preferred embodiment, the device and the process are set up to measure the effect of oxygen on a sample, wherein the oxygen is contained in a gas composition containing nitrogen and carbon dioxide, and the sample is liquid and contains mammalian cells, e.g. human cells, preferably blood cells, e.g. the sample is a whole blood sample. Generally, a gas concentration herein can be referred to as partial pressure.

The device provides a housing that contains an array of wells, e.g. a housing in the form of a microtiter plate having an array of separate wells for receiving separate samples, for measuring the gaseous compound concentration for each well containing a separate sample, preferably without addition of buffer to the sample, and further preferably also measuring the pH in wells provided with a sample aliquot. The process and the device have the advantage of allowing the use of the same set of gas sensors, e.g. two gas sensors, for two or more sample wells, e.g. for all except 2 wells of the array of wells of the housing and with gas sensors in 2 wells. In a further embodiment, the process and the device have the advantage of using a gas source that is set up to provide at least one, preferably two, gas compositions having a pre-determined of at least one gas component, preferably of all its gas components. The embodiments can be used in combination or can be independent from one another. The device and the analytical process using the device are set up for analysing in a sample the optical properties of an analyte that is sensitive to a gas, e.g. an optically detectable analyte that is gas-sensitive, e.g. oxygen-sensitive, $CO_2$-sensitive and/or CO-sensitive. The preferred analyte is haemoglobin or red blood cells.

STATE OF THE ART

Patel et al., Drug Design, Development and Therapy 2018: 12, 1599-1607, for measuring the desorption of oxygen from haemoglobin (Hb) that was purified from red blood cells describe depositing the samples in wells of a 96-well microtiter plate and incubating these samples in ambient air, then deoxygenating the samples by blowing gaseous dry nitrogen over the samples for 2 h while recording absorbances of the Hb in a plate reader serving as a spectrophotometer. The spectrophotometer was set up with a nitrogen inlet that allows filling of the entire spectrophotometer with nitrogen. The measurement parameter was the change in haemoglobin absorbance spectra at defined times after flooding the spectrophotometer with nitrogen, without recording an oxygen dissociation curve which corresponds to the level of saturation of haemoglobin with oxygen versus the partial pressure of oxygen.

Guarnone et al., Haematologica 1995: 80, 426-430 measured absorbances of one blood sample using a spectrophotometer during analysis in a Hemox-Analyzer, which is an automated system for determining the oxyhemoglobin dissociation curve and point of 50% $O_2$-saturation (p50) using a Clark oxygen electrode and concurrent spectrophotometric analysis. The Hemox-Analyzer required strong diluting the blood sample in a buffer in order to allow light absorption measurement of a light path of >10 mm thickness, and to keep the pH at 7.4±0.01.

WO 02/14539 A1 describes small bioreactors formed in wells of a 96-well microtiter plate, each well being equipped with an optically measurable oxygen-sensitive dye and an optically measurable carbon dioxide-sensitive dye.

Sick and Gersonde, Analytical Biochemistry 277-280 (1985) describe a measurement chamber equipped with a controlled gas source, with optical measurement of a single sample carrier arranged in the chamber.

U.S. Pat. No. 10,173,217 B2 describes a microfluidic chip having flow channels that connect storage and reaction vessels for processing an individual liquid sample, with optical detection of labelled compounds bound to analytes.

EP 2 784 481 A2 describes a flow cytometer having a flow cell onto which two lights sources are directed, with a detector for transmitted light and a further detector for scattered light.

Wang and Wolfbeis, Chem. Soc. Rev., 2014, 43, 3666-3761 describe dyes suitable for optically measuring analytes, e.g. oxygen sensitive dyes, carbon dioxide sensitive dyes, pH sensitive dyes, and especially oxygen-sensitive dyes. Dyes described in this publication are preferred as dyes forming an optically detectable gas sensor.

OBJECT OF THE INVENTION

It is an object of the invention to provide an alternative device and an alternative process for analysing the concentration and/or desorption and/or absorption and/or the effect of a gas in or on a sample, preferably in blood, preferably allowing a faster analysis and/or the analysis of at least one, preferably of at least two samples in an array of wells, e.g. arranged in parallel or in series, using common detectors and/or pre-determined gas compositions for all samples.

It is a further object to provide a device and a process using the device for analysing the concentration and/or desorption and/or absorption and/or the effect of gas in a sample, wherein the device and process as the only detector can use a plate reader for spectrophotometric measurements, with no additional detector or electrode being necessary. In this embodiment, the invention shall allow the modification of a plate reader for producing the device according to the invention. A further object is to overcome the limitation of prior art devices that allow analysis of only one sample reacting with a gas or cannot control nor determine the composition of a gas that contacts the sample.

DESCRIPTION OF THE INVENTION

The invention achieves the object by the features of the claims and especially provides a device and a process for analysing the effect of a concentration of a gas on a sample, especially measurement of the gas concentration within the liquid sample, and/or measurement of the effect of the absorption and/or desorption of a gas by the sample, using spectrophotometric detection of a gas-sensitive and optically detectable analyte of the sample while measuring the concentration of the gas in a gas composition that is continuously delivered to each sample well in order to contact the samples with a gas having a pre-determined and/or measured concentration, respectively a pre-determined and/or measured partial pressure in a gas composition. In an embodiment, the gas that is delivered from a gas source to sample wells has a pre-determined composition, preferably the gas source is set up to alternatively deliver at least two gases having different pre-determined compositions at subsequent time intervals, and the device and method are devoid of gas sensors and of measuring gas concentrations, respectively. The analyte can be an indicator that is present in the original sample or that is added to the original sample.

The device comprises a housing which encloses at least one sample well, preferably at least two sample wells, each of the sample wells being in connection to a gas conduit for gas to enter each of the sample wells from a gas conduit and for gas to exit each of the sample wells by a gas conduit, preferably a first gas sensor arranged at the inlet of the gas conduit and a second gas sensor arranged at the outlet of the gas conduit, preferably a gas source connected to the inlet of the gas conduit, the gas source being set up to deliver a gas flow of a constant gas composition, preferably the gas source being set up to deliver a gas flow having an increasing and/or a decreasing concentration of at least one gas component of the gas composition over time, and a spectrophotometer arranged to optically measure each of the sample wells.

Alternatively, the gas source can be set up to deliver at least two gas compositions of different compositions during subsequent time intervals in order to provide at least two different and pre-determined gas compositions at separate, subsequent time intervals to each sample well, with each composition being pre-determined.

Generally, the gas conduit by an entry opening discharges into each well and by an exit opening that is spaced-apart from the entry opening makes gas exit from each well. The entry opening and the exit opening connecting each well to the gas conduit are arranged at a distance from the bottom of the well in order to avoid liquid sample flowing into the gas conduit. Preferably, the gas conduit is formed within the housing.

The at least two sample wells may be connected in parallel to the gas conduit, e.g. connected in parallel by parallel sections of the gas conduit to one inlet of the gas conduit and to one outlet of the gas conduit. Sample wells that are connected to the gas conduit by parallel sections of the gas conduit are preferred for the embodiment, in which the gas source is set up to deliver at least two pre-determined gas compositions, without gas sensors arranged at the inlet or outlet of the gas conduit, and without measuring gas components at the inlet and outlet of the gas conduit, optionally with a gas sensor at the inlet of the gas conduit, preferably with a gas sensor at the outlet of the gas conduit. Preferably, the at least two sample wells are connected in series to one common gas conduit which has one inlet and one outlet, wherein the inlet is connected especially to a gas source that is set up to deliver one, preferably at least two different pre-determined gas compositions. Generally, the gas source can be set up to provide at least two different pre-determined gas compositions one after the other, optionally with a continuous gradient or switching between different gas compositions in one or more steps. Sample wells that are connected by the gas conduit in series are preferred for the embodiment of a gas sensor being arranged at the inlet of the gas conduit and a gas sensor being arranged at the outlet of the gas conduit.

The housing preferably comprises a bottom element in which the at least one sample well, preferably an array of sample wells is formed, and a lid element that can be affixed to the bottom element and closes the sample wells, e.g. subsequent to depositing liquid samples into sample wells. The gas conduit may be formed in a region of the bottom element spaced from the bottom of the wells, e.g. in a region of the bottom element against which the lid element is affixed, e.g. the gas conduit may be formed by a channel formed in the bottom element of the housing, which channel is open on one side, e.g. forming a groove, which is circumferentially closed by a lid element affixed to the bottom portion. Alternatively, the gas conduit may be formed by a groove in the lid element, which groove can be interrupted in lid element areas covering wells.

Preferably, the housing comprises an array of wells, the array comprising sample wells and preferably also at least a first oxygen sensor arranged at the inlet of the gas conduit, e.g. a first gas sensor arranged in one well, which is connected to the inlet of the gas conduit, e.g. directly downstream of the inlet of the gas conduit, and at least a second oxygen sensor arranged at the outlet of the gas conduit, e.g. a second gas sensor arranged in one well, which is connected to the outlet of the gas conduit, e.g. directly upstream of the outlet of the gas conduit, with the gas conduit being in connection with all wells. The element of the housing that comprises the wells can e.g. have an array of 6 wells, of 24 wells, of 8×12 wells or multiples thereof, e.g. in the form of a microtiter plate.

Preferably, the housing between the sample wells is optically non-transparent, e.g. non-transparent for a wavelength irradiated onto a sample well, e.g. non-transparent for a wavelength irradiated from the spectrophotometer onto a sample well, and/or non-transparent for a wavelength emitted out of the sample well.

The first gas sensor that is arranged at the inlet of the gas conduit is arranged upstream of the at least one sample well, preferably between the inlet end of the gas conduit and the at least one sample well. The second gas sensor that is arranged at the outlet of the gas conduit is arranged downstream of the at least one sample well, preferably between the at least one sample well and the outlet end of the gas conduit.

Preferably, both the first gas sensor and the second gas sensor are optical sensors, e.g. containing or consisting of an indicator material, e.g. a dye, preferably a fluorescent dye, which changes its emission in dependence on the gas concentration, e.g. in dependence on the oxygen concentration of the gas composition. Generally preferred, measuring the concentration of the gas in the gas composition is by measuring the signal of a first gas sensor and of a second gas sensor, preferably spectrophotometrically measuring the signal of a first gas sensor and of a second gas sensor, to provide measurements, also referred to as measurement results. An indicator material, e.g. a dye that changes its emission in dependence on the gas concentration is also referred to as a gas-sensitive dye, e.g. a dye that changes its emission in dependence on the oxygen concentration is also referred to as an oxygen-sensitive dye. Preferably, an oxygen-sensitive dye is luminescent or fluorescent and is quenched by presence of oxygen. Exemplary oxygen-sensitive dye catagories are various polycyclic aromatic hydrocarbons, fullerenes, complexes of ruthenium, of osmium, of a lanthanide or of rhenium, porphyrins and metalloporphyrins or various luminescent nanomaterials including quantum dots, all of them immobilized in matrix materials that optionally contain chemical additives. An oxygen-sensitive dye can e.g. be one described by Wang and Wolfbeis, Chem. Soc. Rev., 2014, 43, 3666 — 3761, or haemoglobin.

Oxygen-sensitive dye is preferably arranged in at least two areas of the housing, which preferably are wells of the housing, preferably the first optical sensor comprising or consisting of an oxygen-sensitive dye in a first area, e.g. a well, of the housing that is arranged between the inlet of the gas conduit and any sample well, i.e. downstream of the inlet of the gas conduit and/or directly upstream of any sample well, and the second optical sensor comprising or consisting of an oxygen-sensitive dye in a second area, e.g. well, of the housing that is arranged between all the sample wells and the outlet of the gas conduit, i.e. directly downstream of the sample wells and/or directly upstream of the outlet of the gas conduit. Optionally in addition, an oxygen-sensitive dye can be arranged in at least one additional third area, e.g. a well, of the housing between sample wells. In this embodiment, each gas sensor can consist of an oxygen-sensitive dye, and the sensor signal is detected by the spectrophotometer. Preferably, the oxygen-sensitive dye of all oxygen sensors is the same dye. Preferably, the spectrophotometer consists of a plate reader which is set up to illuminate each of the wells, and to detect light emanating from each of the wells.

In an embodiment, the housing may contain one or two or more gas conduits, each gas conduit connected to sample wells with a first gas sensor, e.g. a first oxygen-sensor, being arranged at the inlet of the gas conduit and a second gas sensor, e.g. a second oxygen sensor, arranged at the outlet of the gas conduit, preferably with a first pressure sensor at the inlet of each gas conduit and a second pressure sensor at the outlet of each gas conduit. One housing may comprise two or more separate gas conduits, each connected to a separate set or array of sample wells. In this embodiment, each separate gas conduit of one housing may be fed with a different gas composition, e.g. with aliquots of one sample being deposited in wells connected to separate gas conduits. A housing containing two or more separate gas conduits may also be called a multi-channel housing, as it allows for an analytical process for analysing the effects of different gas concentrations and/or different gases, each delivered to a separate gas conduit, onto samples deposited in sample wells in parallel.

Especially in the embodiment, in which at least two different pre-determined gas compositions are delivered, one housing may contain at least two separate arrays of sample wells, each connected array being connected in series or in parallel by a separate gas conduit, for deposition of aliquots of the same samples into sample wells of each of the arrays, while the gas source is set up to deliver gas of a different composition to each of the gas conduits connected to one of the arrays. In this embodiment, one spectrophotometer, especially a microtiter plate reader, can be used for measuring, especially concurrently measuring, sample wells containing aliquots of samples that are in contact with different gas compositions, especially subsequent to the same duration of contacting the respective gas compositions. Preferably, aliquots of the samples are deposited in the respective same sample wells of the separate arrays of sample wells such that aliquots of the same sample are deposited in sample wells arranged in the same position along the gas conduit connecting the sample wells of the separate arrays. Preferred pre-determined gas compositions can contain one pre-determined oxygen concentration in the range of 1 to 10% oxygen, e.g. 2%, 3%, 4%, 5%, 6%, 7%, 8%, or 9% oxygen, e.g. remainder to 100% being gaseous water to saturation, nitrogen, carbon dioxide, carbon monoxide, or a combination of at least two of these.

Further optionally, one housing may contain at least one gas conduit connected to sample wells with a first gas sensor, e.g. a first oxygen-sensor, being arranged at the inlet of the gas conduit and a second gas sensor, e.g. a second oxygen sensor, arranged at the outlet of the gas conduit, preferably with a first pressure sensor at the inlet of each gas conduit and a second pressure sensor at the outlet of each gas conduit, and at least one separate array of sample wells, each connected array being connected in series or in parallel by a separate gas conduit, for deposition of aliquots of the same samples into sample wells of each of the arrays, while the gas source is set up to deliver gas of a different and pre-determined composition to each of the gas conduits connected to one of the arrays.

Optionally, a pH sensor, preferably consisting of a pH-sensitive dye, preferably a fluorescent pH-sensitive dye, is arranged in at least one sample well, preferably in an additional sample well provided for an aliquot of a sample, which additional sample well is preferably arranged along the gas conduit directly adjacent to a sample well provided receiving an aliquot of the same sample, which sample well is preferably free from an oxygen-sensitive dye and free from a pH-sensitive dye. In this preferable embodiment, the pH sensor signal is detected by the spectrophotometer. A pH-sensitive dye can e.g. be BCECF. Further optionally, a carbon-dioxide sensor, preferably comprising or consisting of a carbon-dioxide sensitive dye, is arranged in at least one sample well, preferably in an additional sample well provided for an aliquot of a sample, which additional sample well is preferably arranged along the gas conduit directly adjacent to a sample well provided receiving an aliquot of the same sample, which sample well is preferably free from an oxygen-sensitive dye and free from a pH-sensitive dye. In a preferable embodiment, the carbon-dioxide sensor signal is detected by the spectrophotometer.

The spectrophotometer, which preferably is a microtiter plate reader, is set up to illuminate the sample wells of the housing and to detect radiation emanating from the sample wells and/or to detect radiation absorbed by the sample wells, and in preferred embodiments, the spectrophotometer is set up to irradiate areas of the housing in which the first oxygen sensor and/or the second oxygen sensor are formed by an oxygen-sensitive dye, and to measure emission from these areas, which areas preferably are wells in the housing. Preferably, the spectrophotometer is set up for illuminating the sample wells with excitation light at two different wavelengths, one after the other, and to measure radiation emanating from the sample wells for each of the wavelengths illuminated onto a sample well. The light for illuminating the sample wells has a wavelength that is absorbed by the sample, and the spectrophotometer can be set up for measurement of radiation emanating from the sample wells and for determination of an optical property of the sample under illumination and/or without illumination, e.g. for determination of absorption or determination of fluorescence, or determination of luminescence. Accordingly, for measuring light emanating from the sample wells for determination of fluorescence, the light for illuminating sample wells has an excitation wavelength suitable for the sample. For use in analysing liquid samples containing haemoglobin as the analyte, e.g. whole blood samples, the spectrophotometer is e.g. set up to irradiate the wells containing an oxygen-sensitive dye with excitation light of 543 nm and to measure emission emanating at 653 nm, e.g. with a time delay of 6 μs for an integration time of 60 μs for determining fluorescence for this dye, and the spectrophotometer is set up to illuminate sample wells containing the blood samples e.g. at 415 nm to measure absorption at this wavelength, and to separately illuminate the sample wells at 431 nm and to also measure ab sorption at this wavelength.

This embodiment has the advantage of comprising and using a spectrophotometer, which preferably is a microtiter plate reader, as a component of the device of the invention. A preferred microtiter plate reader has a light source and a light detector coupled to optics which are set up to illuminate or irradiate, concurrently or sequentially, wells of a housing which has an array of wells, and to measure light emanating from the illuminated, respectively irradiated wells, or non-irradiated wells, for determination of fluorescence for wells containing a fluorescent dye or for determination of luminescence for wells containing a luminescent compound, and/or for determination of absorption for an absorbing sample, e.g. containing haemoglobin.

Preferably, the spectrophotometer is set up to measure light emanating from sample wells, and preferably is also set up to measure emission from a first oxygen sensor and/or from a second oxygen sensor, each formed by an oxygen-sensitive dye arranged in a well of the housing, further preferably also set up to measure emission from a pH sensor formed by a pH-sensitive dye arranged in a well of the housing, and further preferably also set up to measure emission from a carbon dioxide sensor formed by a carbon dioxide-sensitive dye arranged in a well of the housing, each of these at least two times, with a temporal delay between measurements. The spectrophotometer preferably is connected to a computer which is set up for calculating e.g. absorption and/or fluorescence from the measurements of emanating light. More preferably, the device is set up to deliver a gas flow of a constant gas composition or a gas flow having an increasing and/or a decreasing concentration of at least one component of the gas composition over time during and/or between measurements. The device can be set up to deliver a gas flow having an increasing concentration of at least one component of the gas composition, followed or preceded by a gas flow having a decreasing concentration of at least one component of the gas composition over time during and/or between measurements. Therein, the increasing or decreasing concentration of the at least one component can be a stepwise or a continuous change of concentration. Generally herein, the gas is a component of a gas composition, e.g. air, the component of the composition having an increasing or decreasing concentration over time during and/or between measurements. The gas component can e.g. be one component selected from oxygen, carbon dioxide, carbon monoxide, nitrogen, a noble gas, a vapour or an aerosolized compound, or a combination of at least two of these components. The temporal delay between measurements can e.g. be 1 s to 60 s, e.g. 30 to 45 s, with at least 2, preferably at least 10 or at least 20 or at least 30 measurements of emission from all wells.

It was found that a gas conduit that connects in series all wells between the first gas sensor and the second gas sensor, e.g. a gas conduit that connects in series a well containing the first gas sensor and at which the gas inlet is arranged, sample wells arranged downstream of the first gas sensor, to a well containing the second gas sensor and at which the gas outlet is arranged, in the sample wells generates a gas composition the oxygen concentration of which corresponds to the gas concentration value, which preferably is the oxygen concentration value, of an interpolation between the gas concentrations, e.g. oxygen concentrations measured by the first gas sensor and by the second gas sensor. Accordingly, the device can be set up to determine the oxygen concentration in each sample well by interpolating the gas concentrations, e.g. oxygen concentrations measured by the first gas sensor and by the second gas sensor, especially for equal sample volumes in each sample well and equal kinds of liquid samples in each well, e.g. all liquid samples being one of whole blood, red blood cell concentrates, purified haemoglobin, cell culture samples, e.g. cultivated endothelial cells or epithelial cells, chemicals, a sample originating from an animal, from a plant or from a microbe, or any other sample to be analysed. In an embodiment in which predetermined gas compositions are delivered from the gas source and the device is devoid of gas sensors, respectively the process is devoid of measuring gas concentrations using gas sensors, the process measuring sample wells only, the gas concentration has been found to equilibrate along the array of sample wells connected by the gas conduit, especially for sample wells connected in parallel or in series by one gas conduit, such that the gas concentrations correspond to those of the gas composition delivered by the gas source. It was found that e.g. for 32 sample wells connected by one common gas conduit in series in a 96-well array of a microtiter plate, each well having a gas volume of 250 μL and containing a 15 μL blood sample, a gas flow of 1 to 20 mL/min for approx. 5 min is sufficient for equilibration to the same gas composition corresponding to the pre-determined gas composition delivered to the inlet of the gas conduit.

Preferably, the device comprises a gas conditioning device which is set up to temperature-control the gas to have a temperature at or above the temperature of the housing, preferably in combination with a device for controlling the humidity of the gas to saturation, in order to avoid drying of the liquid samples contained in sample wells.

The sample can be whole blood suspected of containing a compound that enhances or decreases the absorption and/or desorption characteristics for oxygen, which compound can be a pharmaceutical active agent, a toxin, a narcotic, a drug or a doping agent, e.g. in a blood sample originating from a person, e.g. a patient under medication or requiring medication, or an athlete, or originating from an animal.

Preferably, the spectrophotometer is a microtiter plate reader. Optionally, the device of the invention comprises a closure element for closing an opening of a measuring chamber of a microtiter plate reader subsequent to arranging the housing inside its measuring chamber. The closure element has a size adapted to close the opening of the measuring chamber of a microtiter plate reader against ambient light and ambient temperature, and the closure element accommodates at least a gas feed line connected to the inlet of the gas conduit, and optionally accommodates an exhaust gas line connected to the outlet of the gas conduit. The closure element e.g. accommodates a gas feed line or a gas line in through-holes. Optionally, the closure element has only one through-hole for only accommodating one gas feed line, e.g. in an embodiment in which the outlet of the gas conduit is open to allow exiting of the gas flow directly, e.g. into the environment or into the measuring chamber.

In a process for producing the device of the invention, a microtiter plate reader is provided, a housing comprising sample wells connected by a gas conduit with its inlet connected to a gas source, and comprising a first gas sensor and a second gas sensor, preferably each embodied by an oxygen-sensitive dye.

The sample wells can have a tapering inner bottom surface, e.g. conically or curved, and the process may comprise the step of arranging sample liquid in the center of the tapering inner bottom surface by directly depositing the sample liquid in the center of the tapering surface, optionally with centrifuging the housing for moving sample liquid into the center of the tapering surface.

Preferably, the sample wells have a flat inner bottom surface, and the device is in combination with a stamp having a flat front surface. In the process, a liquid sample of a small volume, e.g. 8 to 30 µl, or 10 to 20 µl, can be deposited as a droplet on the flat bottom surface of the well and can be spread into a thin film by moving the stamp front surface against the bottom surface of the well. It was found that for whole blood as the sample liquid, moving the flat front surface of a stamp against the flat bottom well surface generates a uniform sample film, e.g. for a 15 µl whole blood droplet in a well of a 96-well microtiter plate (round bottom surface diameter of ca. 6 mm) a film having a thickness of approximately 2 cell layers was generated, which liquid film remained spread out after removing the stamp. The stamp front surface preferably has a diameter fitting into a well, optionally with a gap to the side wall of the well of e.g. 0.1 to 1 mm. Preferably, the front surface of the stamp is of an inert material, e.g. polytetrafluoro ethylene (Teflon), or of metal, more preferably of stainless steel.

Further optionally, the device of the invention comprises a stamping device having one stamp for each sample well in an array of stamps that corresponds to the array of sample wells, e.g. excluding wells containing an oxygen sensor, a pH sensor or a $CO_2$ sensor, or any other type of sensor.

Preferably, the device comprises a first pressure sensor set up for recording the gas pressure at the inlet of the gas conduit, and a second pressure sensor set up for recording the gas pressure at the outlet of the gas conduit. The first and second pressure sensors can be embodied by a pressure sensor for ambient air pressure and a pressure sensor set up to determine the pressure difference between the inlet and the outlet of the gas conduit, the latter of which can be the overpressure of the gas source to ambient pressure, or the vacuum generated by a suction pump connected to the outlet of the gas conduit.

Preferably, the spectrophotometer is connected to a computer which is set up for analysing the measurement results of the detected light emanating from sample wells, preferably measurement results for determining absorption determined from illuminating the sample wells with light at two or more different wavelengths and measuring emanating light. For the oxygen-sensitive dye and optional further sensor dyes, the spectrophotometer is preferably set up to irradiate the sensor dye at an excitation wavelength and to measure emission. Generally preferably, the computer is set up to determine emission and/or absorption for an empty well, and to substract empty well measurements from sample well measurements, respectively from sensor dye measurements, for generating measurement results. Generally preferred, the device is set up for temperature control of the housing and for temperature control of the gas delivered into the inlet of the housing, e.g. control to the same temperature or control of the gas delivered to the inlet of the gas conduit to a higher temperature than the temperature of the housing, preferably, especially for liquid samples, comprising a conditioning device that is set up for saturating the gas composition delivered to the inlet of the gas conduit with humidity.

For a liquid sample containing hemoglobin, e.g. a whole blood sample, the computer can be set up to determine the as ((A−Maximum (Abs))/(Minimum (Abs)−Maximum (Abs))×Z, wherein $Abs=A_{431nm}/A_{415nm}$, and the functional haemoglobin (Hb) fraction Z=100%−(MetHB+COHb), wherein MetHb is methylated haemoglobin and COHb is CO-bound haemoglobin.

The oxygen concentration is also referred to as oxygen partial pressure $PO_2$. Generally preferably, the computer is set up for the following calculations:

The maximum oxygen partial pressure $maxPO_2$=initial Vol.-% $O_2$×(barometric pressure difference between gas conduit and outside well), wherein the initial Vol.-% $O_2$ is the oxygen contents of the gas composition entering the inlet, e.g. the gas composition provided by the gas source. Outside well pressure is environmental pressure.

The oxygen concentration ($PO_2$) measured by the first oxygen sensor can be determined as inlet-$PO_2$=(signal of first oxygen sensor/maximum signal of first oxygen sensor)−$1/K_{first\ oxygen\ sensor}$, and outlet oxygen concentration outlet-$PO_2$=(signal of second oxygen sensor/maximum signal of second oxygen sensor)−1)/$K_{second\ oxygen\ sensor}$, wherein $K_{first\ oxygen\ sensor}$ is a calibration factor for the first oxygen sensor, $K_{first\ oxygen\ sensor}$=((maximum signal of first oxygen sensor/minimum signal of first oxygen sensor)−1)/max $PO_2$, and $K_{second\ oxygen\ sensor}$ is a calibration factor for the second oxygen sensor, $K_{second\ oxygen\ sensor}$=((maximum signal of second oxygen sensor/minimum signal of second oxygen sensor)−1)/max $PO_2$, with max $PO_2$ being the maximum partial pressure of $O_2$ in the gas composition.

The local oxygen partial pressure of the gas composition in each sample well, local $PO_2$, can be determined by linear interpolation as local $PO_2$=inlet-$PO_2$+((position of sample well along gas conduit/total number of sample wells along gas conduit)×(inlet-$PO_2$−outlet-$PO_2$)).

Preferably, the computer is set up to determine the Hill-function $SO_2$ by linear regression analysis as $SO_2$=(Z× $PO_2$^a)/(C^a+$PO_2$^a),
using the least square method for curve fitting,
for determining P50=C, and the Hill coefficient=a.

The process according to the invention has the advantage that it does not require adding a buffer compound to the sample. The process can therefore be carried out on the sample directly, e.g. without diluting and/or without adding a buffer to the sample.

The invention is suitable for use in monitoring patients, especially intensive care patients, e.g. for measuring oxygen affinity of blood samples for analysing the effect of medicaments, for use in quality control of blood preserves, for use in functional testing of erythrocytes in polycythemia, e.g. testing for hemoglobinopathy, for use in analysing hemoglobinopathy in newborns, for use in doping controls, e.g. by determining a shift of P50, for use in controlling athletes, e.g. for determining oxygen binding characteristics, and/or for use in toxicology, pharmacology.

The invention is now described in greater detail by way of examples and with reference to the figures, which show in
FIG. 1a a schematic overview of a device according to the invention,
FIG. 1b a schematic of an embodiment with multiple gas conduits of a housing for use in the invention, FIG. 2a a housing for use in the invention, FIG. 2b shows an enlarged partial cross-section of a part of the housing of FIG. 2a, FIG. 2c shows a micrograph of a blood sample spread out in a sample well, FIG. 3 shows measured (fluorescence lifetime of an oxygen-sensitive dye forming an oxygen sensor in the device of the invention) vs. calculated $PO_2$, FIG. 4 shows measured linear oxygen concentrations in sample wells connected by a gas conduit in series in the device of the invention, FIG. 5 shows absorption spectra for whole blood under different gas flow, and FIG. 6 shows gas absorption measurements of a blood sample in one sample well under a decreasing oxygen partial pressure in nitrogen, FIG. 7 shows a mean of several oxygen dissociation curves (continuous line) and standard deviation (vertical error bars)

Figures 1A, 1B:
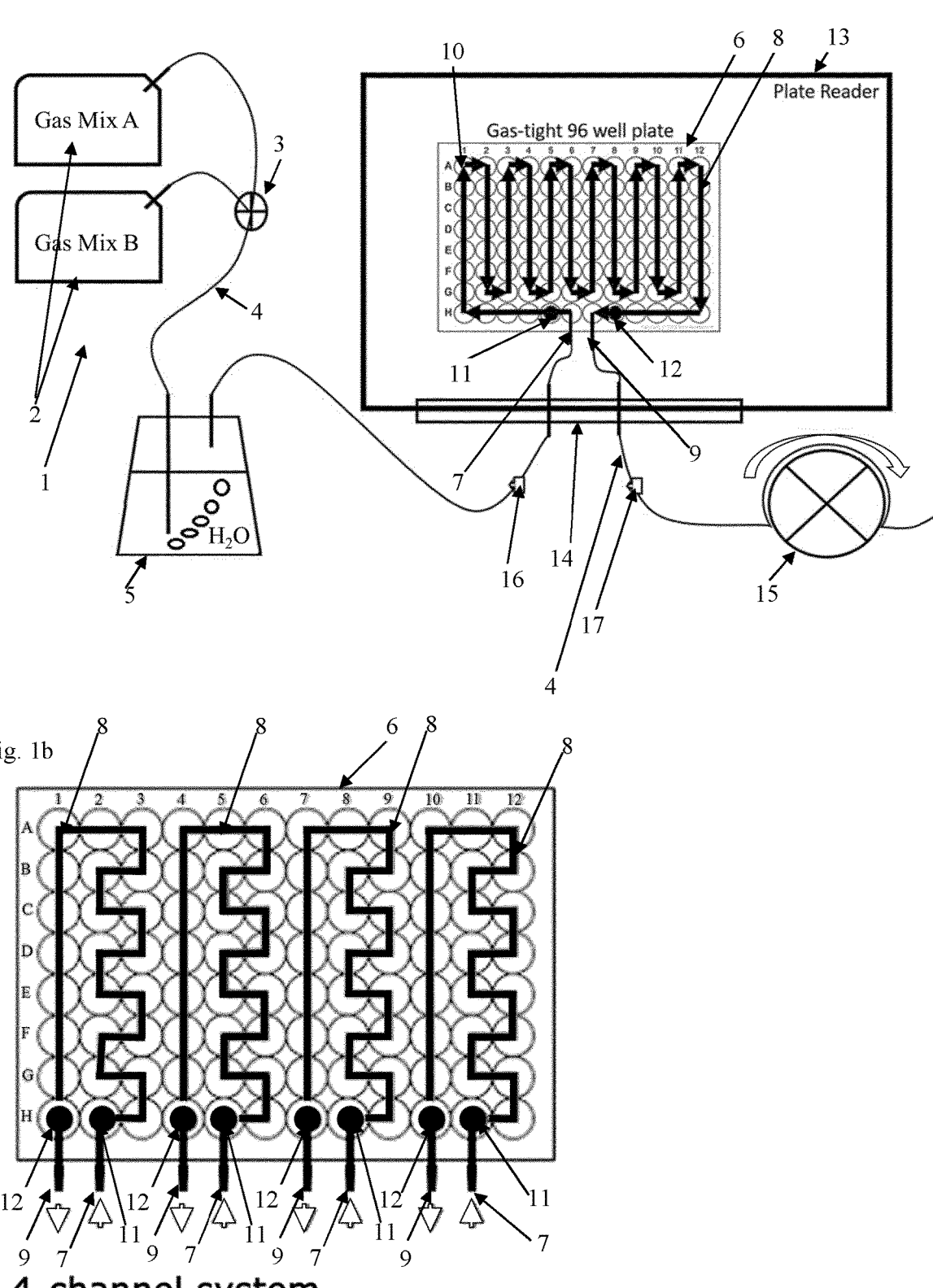

FIG. 1a shows a gas source 1 having two reservoirs 2 for gas components and a mixing valve 3 which is connected by a gas line 4 to a conditioning device 5 that temperature-controls the gas to a temperature of the temperature of the housing 6 or to a temperature above, e.g. 1 or 2° C. above the temperature of the housing 6. From the conditioning device 5, the gas line 4 is connected to an inlet 7 of a gas conduit 8 arranged within the housing 6, the gas conduit 8 leaving the housing 6 at outlet 9. The housing 6 contains 96 wells in a 8×12 array of wells, 92 of which are sample wells 10, a first gas sensor 11 is arranged in one well between the inlet 7 and the sample wells 10, and a second gas sensor 12 is arranged in one well between the sample wells 10 and the outlet 9. The first gas sensor 11 and the second gas sensor 12 consist of the oxygen-sensitive dye arranged on the bottom of their well. The gas conduit 8 from the first gas sensor 11 meanders along all wells 10 to the second gas sensor 12, connecting all sample wells 10 in series between the first gas sensor 11 and the second gas sensor 12.

The housing 6 encloses the openings of the wells 10 so that the gas entering the inlet 7 flows along the first gas sensor 11, along all of the sample wells 10, and along the second gas sensor 12. The housing 6 is arranged in the measuring chamber of a plate reader that forms the spectrophotometer 13. An entry opening of the spectrophotometer 13 is light-proof closed by a closure element 14, through which the gas line 4 is arranged for connection with the inlet 7 and a gas line 4 for connection of the outlet 9 to a suction pump 15. For measuring the pressure drop along the gas conduit 8, a first pressure sensor 16 is arranged in the gas line 4 leading to the inlet 7, and a second pressure sensor 17 is arranged in the gas line 4 between the outlet 9 and the suction pump 15.

FIG. 1b shows an embodiment of one housing 6 that contains 4 separate gas conduits 8, each with an individual inlet 7 for gas with a first gas sensor 11 arranged at the inlet 7, and an individual outlet 9 for gas with a second gas sensor 12 arranged at the outlet 9.

Figures 2A, 2B, 2C:
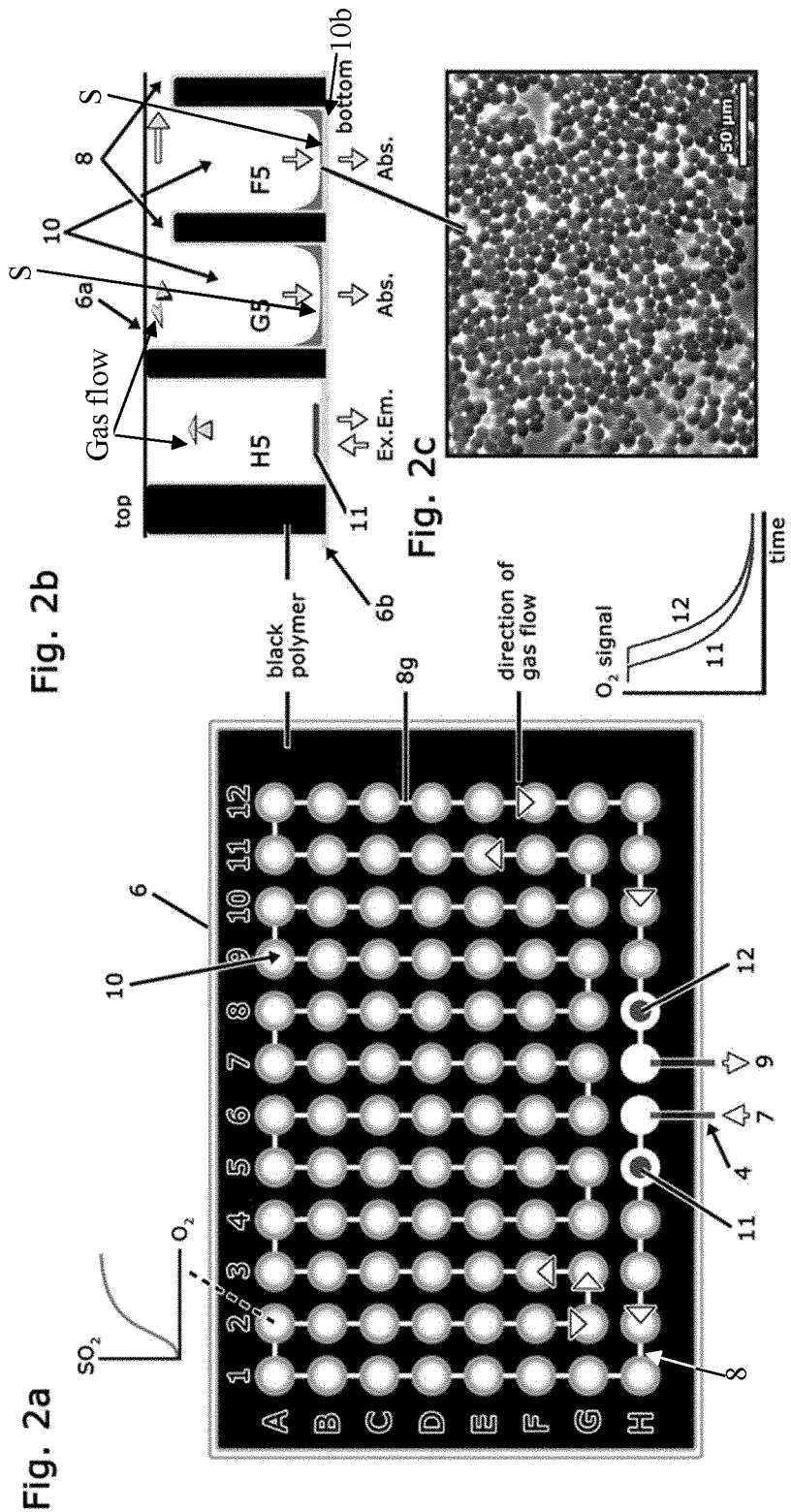

FIG. 2a in greater detail shows a housing 6 in top view with the array of the sample wells 10, a first gas sensor 11 between the inlet 7 and the sample wells 10, and a second gas sensor 12 between the sample wells 10 and the outlet 9. The gas conduit 8 that connects the sample wells 10 is arranged adjacent the plane of the top openings of wells 10 in the microtiter plate that forms a bottom element 6b with a lid element 6a in the form of an air-tight plastic cover of the housing 6.

FIG. 2b shows an enlarged cross-section of part of the housing 6 (wells H5, G5 and F5) with a bottom element 6b containing sample wells 10, a well (well H5) containing the first gas sensor 11 adjacent to the inlet 7, and the gas conduit 8 formed as a groove 8g in the upper portion and sealed by a lid element 6a. The gas conduit 8 does not directly connect well H5 to well G5 but via intermediate wells. In this embodiment, the gas conduit 8 is arranged in the bottom element 6b and opposite from the bottom 10b of sample wells 10. The direction of the gas flow is schematically indicated by arrows. As indicated by "Abs.", measurement can be absorption measurement through a sample S arranged on the bottom 10b of wells, and measurement of oxygen sensors 11, 12 can be by excitation irradiation "Ex." and detection of emission "Em.".

FIG. 2c shows a micrograph of a blood sample spread out on the bottom 10b. This shows that a sample volume of 15 μl can be spread out to a stable thin layer by moving a metal stamp against the sample that was pipetted onto the bottom 10b.

Figure 3:
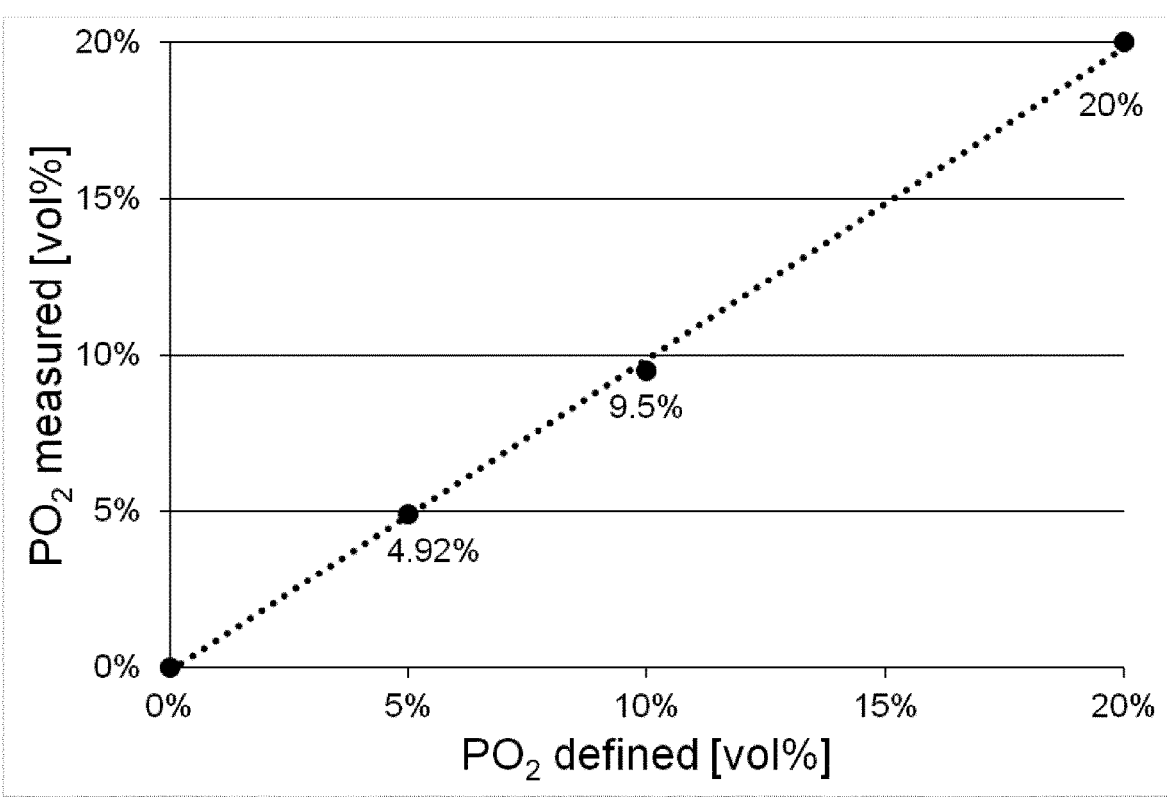

FIG. 3 depicts measurement of $PO_2$ fluorescence lifetime of the oxygen-sensitive dye 200000023 SP-PSt3-NAU-D5-YOP, available from PreSens, Regensburg, Germany, in a plate reader used as the spectrophotometer in relation to calculated values, showing a highly linear correlation (Concordance correlation coefficient 0.999).

Figure 4:
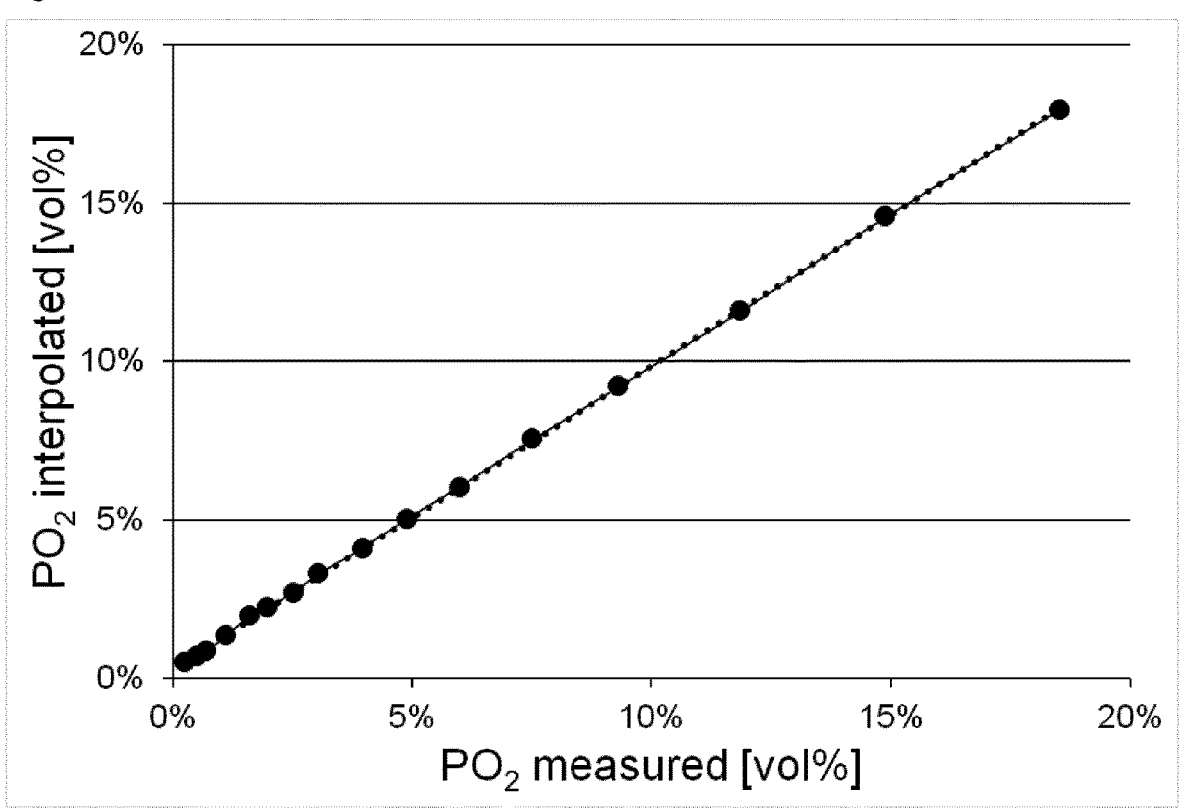

FIG. 4 shows the results of oxygen concentration measurements as partial pressure ($PO_2$) with first and second oxygen sensors 11, 12 and an additional third oxygen sensor that was arranged in a sample well (well G12 in the microtiter plate element of the housing of FIG. 2a) under a gas having decreasing oxygen concentration, in relation to oxygen partial pressures calculated. This shows that also for a gradient of a gas component in the gas flowing along the gas conduit 8 through all the sample wells 10 in series, the gas concentration, exemplified by the oxygen partial pressure, can be interpolated from the signals of the first gas sensor 11 and the second gas sensor 12.

Example: Measurement of Oxygen Absorption by Whole Blood

In a device as shown in FIG. 2a, as a representative of a sample containing an oxygen sensitive analyte, whole blood was deposited into a sample well and spread out on the bottom of the sample well using a stamp. As a gas, a gas mixture containing an oxygen concentration of %, a carbon dioxide concentration of 5% and 75% nitrogen, for measuring the oxygenated state ($HbO_2$) of haemoglobin was used and after flushing with nitrogen and carbon dioxide (5%), nitrogen and carbon dioxide (5%) was used for measuring the deoxygenated state (Hb). The gas was introduced into the gas conduit 8 of the housing 6. Measurements of first and second oxygen sensors 11, 12 were by irradiating with excitation wavelength of 543 nm and detecting emission at 653 nm every 1 min in a plate reader (Tecan) forming the spectrophotometer. Sample wells were illuminated at 415 nm and, separately at 431 nm, recording absorption every 1 min. Saturation ($SO_2$) was calculated using the absorption ratio $A_{431nm}/A_{415nm}$, which ratio is independent of the sample volume.

Figure 5:
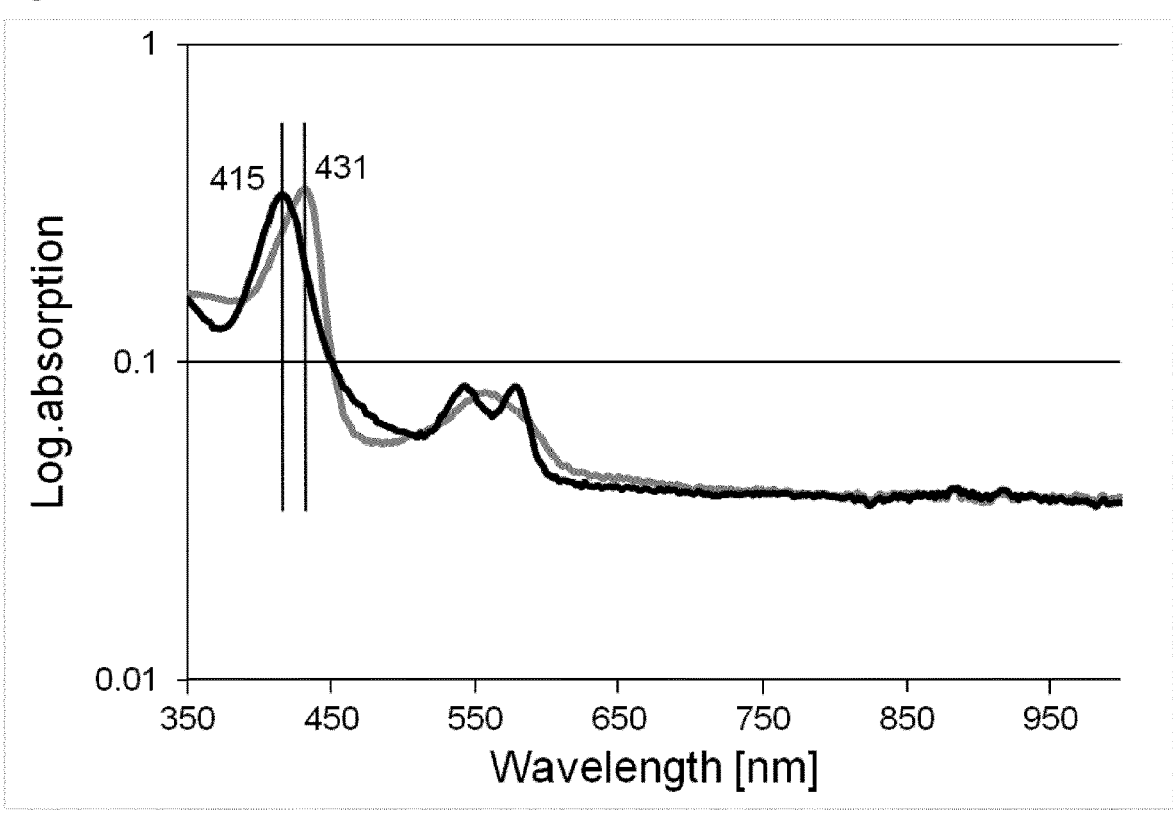

The haemoglobin absorption spectrum of FIG. 5 shows typical curves, indicating that the device and process of the invention are suitable for such measurements.

Figure 6:
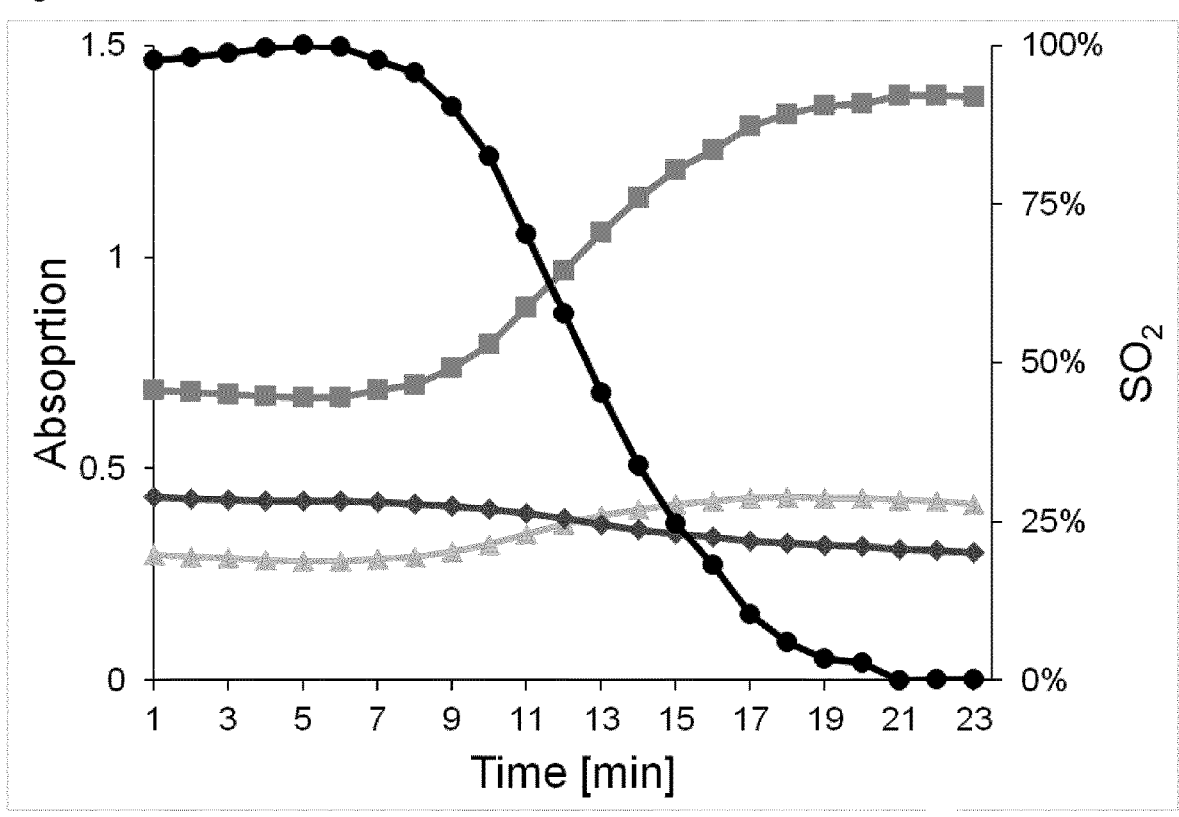

Using a mixing device, the gas had an oxygen concentration decreasing from an initial 20% to 0% in nitrogen over 20 to 25 min. Measurements were made on a whole blood sample spread out on the flat bottom of one sample well (e.g. sample well position A6 of FIG. 2a) of a housing according to FIG. 2a. In addition to measuring the oxygen concentration by a first oxygen sensor and a second oxygen sensor, the pH was measured using a pH-dependent dye in an adjacent sample well covered with a sample aliquot. The housing was temperature-controlled to 37° C. in the measuring chamber of the plate reader. After 15 min, a plasma pH drift in the blood film by −0.05 pH units was detected. The pH drift is considered to be within a physiological range. This small pH drift that occurs after 15 min shows that the process according to the invention can be performed without buffer added to the sample, especially when determining the p50 and/or the ODC within 15 min of the analysing process. FIG. 6 shows the results (▲=absorption at 431 nm, ◆=absorption at 415 nm, ■=ratio of absorption at 431 nm/absorption at 415 nm, ●=oxygen saturation), and also the p50 of the oxygen dissociation curve (ODC) that is determined at 15 min.

Effects of storage of blood samples at 0 to 5° C. was evaluated via repeated blood gas analysis of aliquots. Within 8 h of storage, plasma pH, COHb and MetHb did not change, whereas potassium levels and lactate slightly increased, and glucose and the anion gap slightly decreased. This shows that the process can reliably be performed using blood samples that were stored at 0 to 5° C. for up to 8 h.

Figure 7:
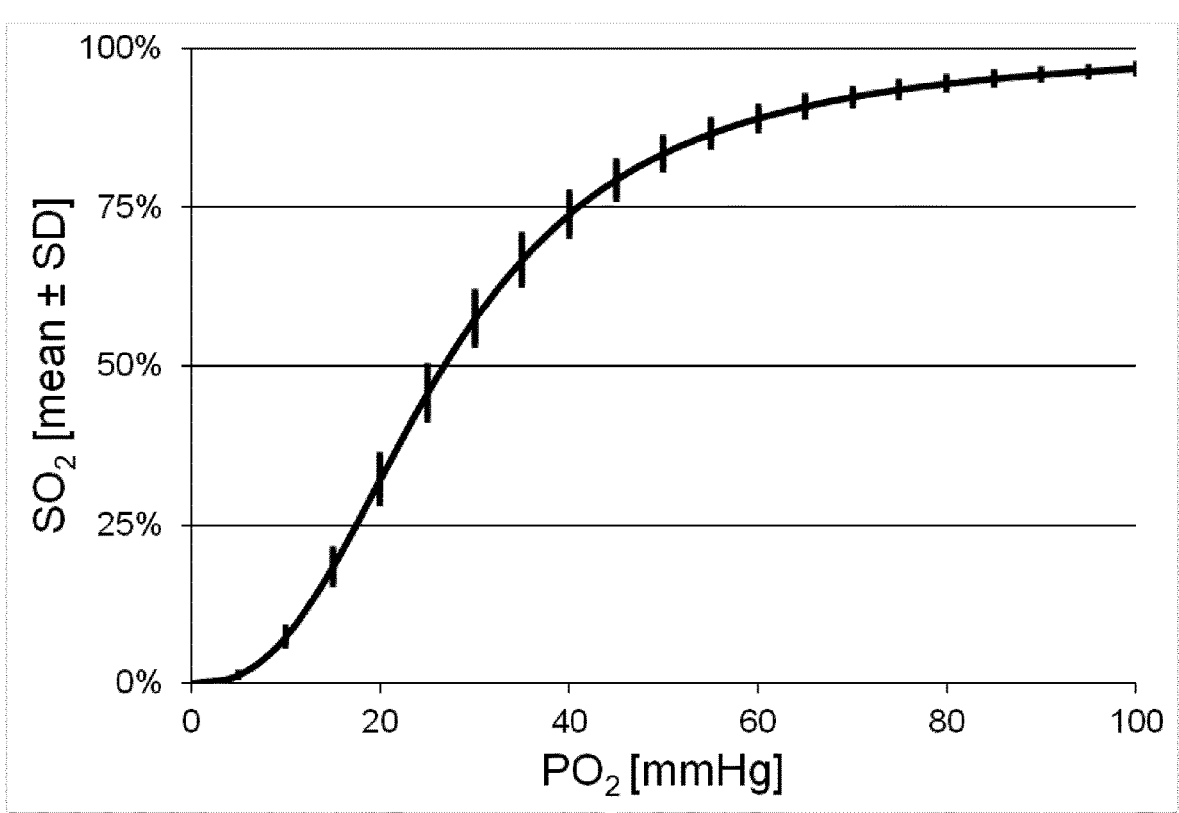

When testing the intra-assay variability, it was found that within one housing comprising a microtiter plate (94 sample wells), the p50 values of the ODCs of whole blood are scattered with a mean Standard Deviation (SD) of 1.2 and a mean Coefficient of Variation (CV) of 0.04. This shows a fairly high precision and low intra-assay variability for the analytical process of the invention. This intra-assay variability, however, was found to strongly depend on data definition: it further strongly decreases with decreasing sample size, i.e. by pre-averaging the results from three (SD=0.72), six (SD=0.57). FIG. 7 shows the intra-assay variability is with the arithmetic means of several points (94 sample wells). It can be seen that SD is considerably higher in the steep part of the slope, levelling off in the flat, asymptotic ranges. Currently, it is therefore preferred to initiate the analytical process at oxygen concentrations ($PO_2$) of at least 40 or at least 60 mm Hg, preferably at least 70 or at least 80 mm Hg.

It was found that the device and method of the invention provided for a very low inter-assay variability of measurement results when the process was performed by different laboratory workers. Currently, this very low inter-assay variability, and respectively a high reproducibility of the process is believed to be based on the temperature control of the housing, the temperature control of the gas delivered into the inlet of the housing, and the measurement of the gas concentration by the first gas sensor and the second gas sensor and measurement of the analyte with no or only a short delay, and on the set up of the device and the use of internal standard solutions.

A comparison of oxygen absorption measurement using standard haemoglobin solution (Equil QC 463) with a Hemox Analyzer (TCS Scientific Corp., USA) using a 100-fold dilution of the standard haemoglobin in accordance with the manufacturer's instruction for 118 sample measurements, each measurement lasting 30 min, gave a mean of 26.4±1.33 mm Hg, and using the device according to the invention using 10-fold diluted standard haemoglobin solution, in 3 runs, each for 94 sample wells in parallel containing triplicates of each sample lasting 30 min, gave a mean of 24.60±0.72 mm Hg (SD). In the set-up of the device according to the invention, a 100-fold dilution due to the thin film of the small sample volume gave no signal, and therefore a higher concentration of the standard haemoglobin solution was used. This also shows that the invention has the advantage of allowing the use of an undiluted, i.e. original, whole blood sample to be analysed, avoiding an influence of added reagents, e.g. avoiding dilution effects on the sample.

As a further comparison, blood samples of a female patient diagnosed with severe polycythaemia (Hb=18 g/dl) and a suspected high oxygen affinity hemoglobinopathy (p50<23 mm Hg) were tested. Aliquots of the blood samples were simultaneously analysed with the Hemox Analyzer. Importantly, p50 determinations were performed synchronously (24 h after venipuncture). A second blood sample from a healthy control person was analysed according to Mayo Clinic guidelines. Using the device according to the invention, a total of 120 ODCs from patient's blood and 72 ODCs from the control person were measured. When defining a result to be the mean of 3 sample wells, 40 independent p50 determinations were made. In the patient, p50 was 27.2±1.13 mmHg (mean±SD) and thus slightly elevated (right-shift of ODC) compared with the healthy control (25.8±0.88 mm Hg).

Analyses of blood sample aliquots with blood gas analyzer, which is generally known to give an estimate of p50 with low accuracy only, the p50 of the patient was slightly increased over the healthy control, whereas both results were in the normal range.

In the Hemox Analyzer only one result was provided: p50=28.7 mmHg in the patient and p50=26.3 mmHg in the healthy control. This is the third independent and standard method to exclude a high oxygen affinity haemoglobinopathy in this patient. Further, this comparison shows that the device and process of the invention provide an accurate result in a shorter time.

Figure 8:
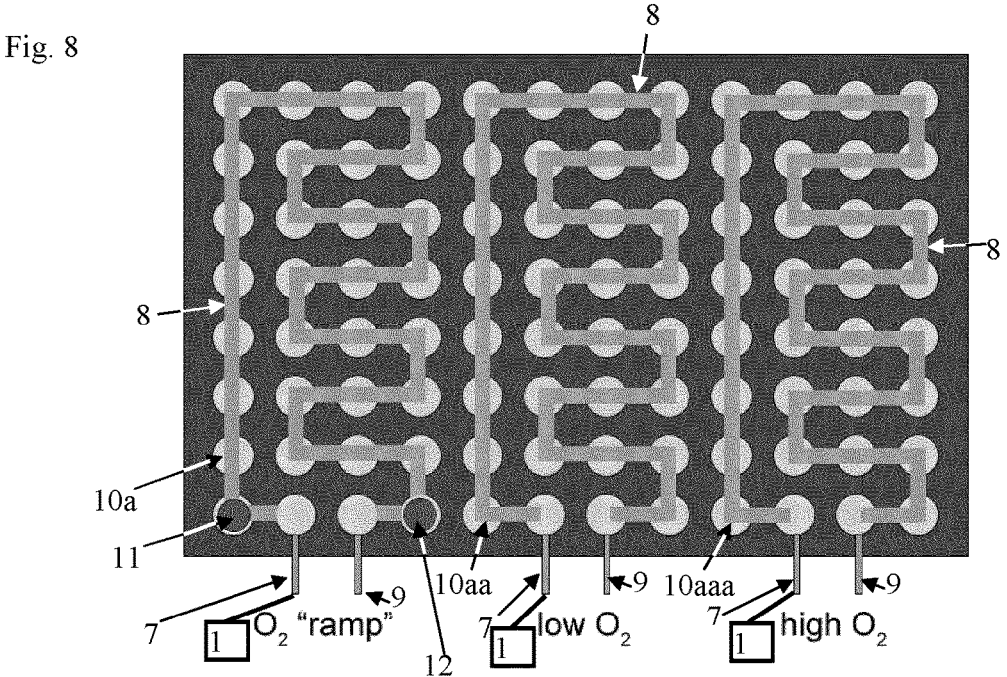
FIG. 8 shows an exemplary device.

FIG. 8 shows three separate arrays of sample wells contained in one housing, each array connected by a separate gas conduit that is connectable to a gas source. The array of sample wells 10a contains a first gas sensor 11 in one well that is arranged at the inlet 7 of the gas conduit 8 and a second gas sensor 12 in one well that is arranged at the outlet 9 of the gas conduit 8. The inlet 7 of the array of sample wells 10a is preferably connected to a gas source 1 that is set up to deliver at least two different gas compositions, preferably a continuously changing gas composition, e.g. a changing oxygen concentration ($O_2$ "ramp"). The inlet of the gas conduit connecting the array of sample wells 10aa, and the inlet of the gas conduit connecting the array of sample wells 10aaa are each connected to a gas source that is set up to deliver, preferably to concurrently deliver, different predetermined gas compositions having a stable composition. For example, array of sample wells 10aa can be connected to a gas source providing 3% (low $O_2$) oxygen in water-saturated nitrogen, while parallel array of sample wells 10aaa can be connected to a gas source providing 5% oxygen (high $O_2$) in water-saturated nitrogen. Samples to be tested, e.g. blood samples, are preferably provided as aliquots in corresponding sample wells, e.g. aliquots of one sample are deposited in sample wells having the same distance from the inlet 7 of the gas conduit 8 of each array of sample wells 10aa, 10aaa.

Figure 9:
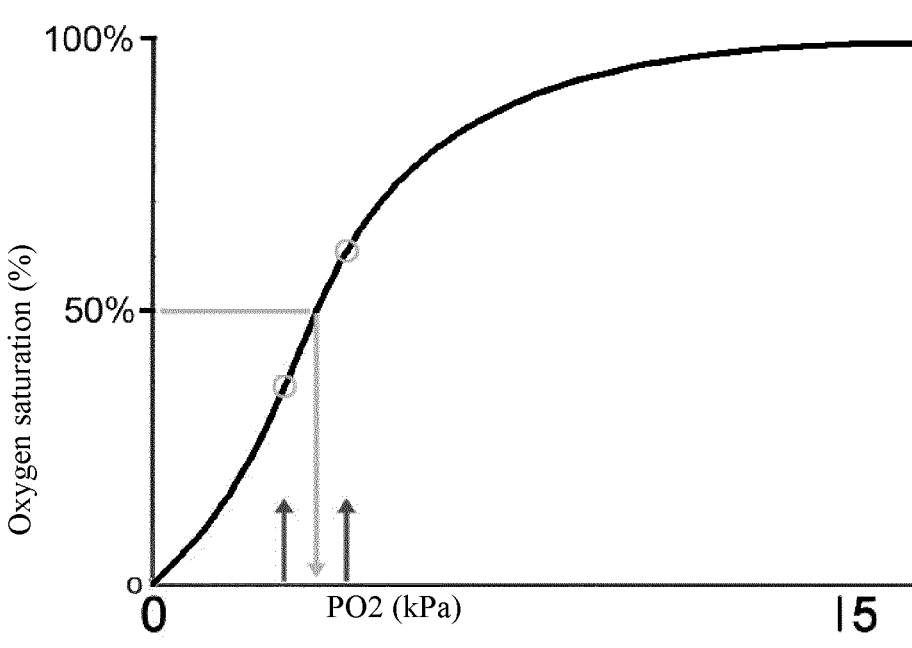
FIG. 9 shows a representation of measurement results obtained for one sample using two pre-determined gas compositions.

FIG. 9 for one sample shows measurements obtained in sample wells of parallel arrays of sample wells 10aa, 10aaa, each of the gas conduits that connect one of the arrays provided with a gas composition having a different oxygen concentration, expressed as oxygen partial pressure (PO2 (kPa)). These two measurements (○) are linearly interpolated or fit into a saturation curve, e.g. into a pre-determined sigmoidal Hill plot for oxygen saturation of hemoglobin, to determine the P50 value. This example shows that measurement of the analyte, herein hemoglobin, in two aliquots of one sample while in contact with different gas compositions can be sufficient for determining the saturation, e.g. the P50 value.

---

Reference numerals:

1 gas source
2 reservoir for gas component
3 mixing valve
4 gas feed line
5 conditioning device
6 housing
6a lid element
6b bottom element
7 inlet
8 gas conduit
8g groove
9 outlet
10, 10a, 10aa, 10aaa sample well
10b bottom of sample well
11 first gas sensor
12 second gas sensor
13 spectrophotometer
14 closure element
15 suction pump
16 first pressure sensor
17 second pressure sensor
S sample

---

The invention claimed is:

1. A device for analyzing the effect of a gas in a sample, the device comprising: a housing enclosing at least one sample well, a gas conduit connected to the at least one sample well configured to permit gas to enter and to exit the at least one sample well, a gas source connected to an inlet of the gas conduit, a concentration device that is configured to determine the concentration of at least one component of the gas, and a spectrophotometer arranged to optically measure the at least one sample well, wherein the spectrophotometer is a microtiter plate reader, the device comprising a closure element adapted to close an opening of a measuring chamber of the microtiter plate reader subsequent to arranging the housing inside the measuring chamber, which closure element accommodates at least a gas feed line connected to the inlet.

2. The device according to claim 1, wherein the concentration device comprises a first gas sensor arranged at the inlet and a second gas sensor arranged at an outlet of the gas conduit.

3. The device according to claim 2, wherein both the first gas sensor and the second gas sensor comprise optical sensors containing an indicator material that changes its emission in dependence on gas concentration.

4. The device according to claim 1, wherein the concentration device comprises or consists of a gas source configured to provide a pre-determined concentration of the at least one gas component, and wherein the at least one sample well comprises an array of at least 2 sample wells which are connected in series to the inlet.

5. The device according to claim 1, wherein the gas source is configured to deliver a gas flow having an increasing and/or a decreasing concentration of the at least one component of the gas over time or a gas flow having a constant concentration of all gas components of the at least one component of the gas over time.

6. The device according to claim 1, comprising a first pressure sensor configured to record gas pressure at the inlet, and a second pressure sensor configured to record gas pressure at an outlet of the gas conduit.

7. The device according to claim 1, comprising a conditioning device configured to temperature-control gas between the gas source and conduit to have a temperature at or above a temperature of the housing and configured to control humidity of the gas to saturation.

8. The device according to claim 1, wherein the at least one sample well comprises at least two sample wells connected in series to the inlet and an outlet of the gas conduit.

9. The device according to claim 3, wherein the at least one sample well comprises a dye which changes its emission in dependence on gas concentration, which dye is an oxygen-sensitive dye, a pH sensitive dye, and/or a carbon dioxide-sensitive dye, and the spectrophotometer is configured to optically measure the first gas sensor and the second gas sensor.

10. A device for analyzing the effect of a gas in a sample, the device comprising: a housing enclosing at least one sample well, a gas conduit connected to the at least one sample well configured to permit gas to enter and to exit the at least one sample well, a gas source connected to an inlet of the gas conduit, a concentration device that is configured to determine the concentration of at least one component of the gas, and a spectrophotometer arranged to optically measure the at least one sample well, wherein the at least one sample well comprises an array of sample wells, wherein the housing comprises a bottom element in which the array is and a lid element affixable to the bottom element configured to close the sample wells, and wherein the housing contains at least two separate gas conduits, each gas conduit connected to a separate array of sample wells in series and each gas conduit provided with a first gas sensor arranged at the inlet of the gas conduit and with a second gas sensor arranged at the outlet of the gas conduit.

11. The device according to claim 10, wherein the gas conduit comprises a groove in a region of the bottom element spaced from the bottom of the wells, which groove is configured to be circumferentially closed by the lid element.

12. Device The device according to claim 10, wherein the gas conduit is formed as a groove in the lid element, wherein the groove is interrupted in areas of the lid element covering wells.

13. The device according to claim 12, wherein each gas conduit connecting a separate array of sample wells is connected to a gas source configured to provide a different pre-determined gas composition.

14. A device for analyzing the effect of a gas in a sample, the device comprising: a housing enclosing at least one sample well, a gas conduit connected to the at least one sample well configured to permit gas to enter and to exit the at least one sample well, a gas source connected to an inlet of the gas conduit, a concentration device that is configured to determine the concentration of at least one component of the gas, and a spectrophotometer arranged to optically measure the at least one sample well, wherein the spectrophotometer is connected to a computer configured to analyze light emanating from sample wells at at least one wavelength or at two or more different wavelengths, and to determine absorption for the at least one illumination wavelength, and wherein the computer is configured to determine local oxygen partial pressure of gas in each sample well, local $PO_2$, by linear interpolation in accordance with:

local $PO_2$=inlet-$PO_2$+((position of sample well along gas conduit/total number of sample wells along gas conduit)×(inlet-$PO_2$-outlet-$PO_2$)).

15. A process for analyzing the effect of a gas comprising depositing the at least one sample into one of an array of at least two sample wells contained in a housing, continuously delivering a gas composition containing a gas to the array of sample wells through a gas conduit in serial connection with each sample well, and spectrophotometrically concurrently measuring each sample well containing an aliquot of samples while in contact with gas, wherein the at least one sample is a whole blood sample deposited as a droplet on a flat bottom surface of one of the at least two sample wells and is spread into a thin film by moving a stamp front surface against the bottom surface of the one of the at least two sample wells, and determining absorption and/or desorption of gas by the whole blood sample while at least one component of the gas composition has an increasing and/or a decreasing concentration, stepwise or continuous, over time during and/or between measurements.

16. The process according to claim 15, comprising spectrophotometrically detecting a gas-sensitive and optically detectable analyte of the at least one sample deposited in the at least one sample well at an inlet and outlet of a gas conduit connected to the array of sample wells, measuring concentration of a gas by spectrophotometrically measuring signals of a first gas sensor and of a second gas sensor, which each are optical sensors containing an oxygen-sensitive dye, and determining the concentration of the gas in each sample well by interpolating between the measurements of the first gas sensor and of the second gas sensor.

17. The process according to claim 15, wherein aliquots of the at least one sample are deposited in sample wells of the at least two separate arrays, wherein each gas conduit connecting the sample wells of one array is connected to a gas source that delivers a different gas composition, wherein a different constant gas composition is concurrently delivered to each array of sample wells, spectroscopically measuring each sample well, and interpolating between the measurement results obtained for aliquots of one sample.

18. A process for producing a device for analyzing the effect of a gas in a sample, comprising providing a microtiter plate reader as a spectrophotometer, arranging a housing comprising an array of sample wells connected in series by a gas conduit with its inlet connected to a gas source, the housing comprising an oxygen-sensitive dye arranged in a well of the housing as a first gas sensor, which well is arranged between the inlet and sample wells, and comprising an oxygen-sensitive dye arranged in a well of the housing as a second gas sensor, which well is arranged between sample wells and an outlet of the gas conduit, in a measuring chamber of the microtiter plate reader, and arranging a closure element for closing an opening of a measuring chamber, which closure element accommodates at least a gas feed line connected to the inlet of the gas conduit, wherein the gas conduit is formed as a groove in the lid element, which groove is interrupted in areas of the lid element covering wells.

19. A process for producing a device for analyzing the effect of a gas in a sample, comprising providing a microtiter plate reader as a spectrophotometer, arranging a housing comprising an array of sample wells connected in series by a gas conduit with its inlet connected to a gas source, the housing comprising an oxygen-sensitive dye arranged in a well of the housing as a first gas sensor, which well is arranged between the inlet and sample wells, and comprising an oxygen-sensitive dye arranged in a well of the housing as a second gas sensor, which well is arranged between sample wells and an outlet of the gas conduit, in a measuring chamber of the microtiter plate reader, and arranging a closure element for closing an opening of a measuring chamber, which closure element accommodates at least a gas feed line connected to the inlet of the gas conduit, wherein the gas conduit is formed as a groove in a region of the bottom element spaced from the bottom of the wells, and which is a region of the bottom element against which the lid element is affixed, which groove is configured to be circumferentially closed by the lid element.

* * * * *